United States Patent [19]

James

[11] Plant 4,739

[45] Jun. 9, 1981

[54] ALMOND TREE

[75] Inventor: Leonard D. James, 4017 Tully Rd., Modesto, Calif. 95350

[73] Assignees: Leonard D. James; Uldine S. James, both of Modesto, Calif.

[21] Appl. No.: 155,833

[22] Filed: May 30, 1980

[51] Int. Cl.[3] ..... A01H 5/03

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is open, medium size, vigorous, stocky of trunk and branches, both with smooth texture, upright with diverging branches, foliated with medium size, acuminate, acutely pointed, thin, smooth-textured leaves having a crenate, finely serrate margin and small, alternate, green, globose glands, blooms heavily with pink flowers, and is a regular and heavy bearer of large, well-sealed, well-distributed nuts having large kernels.

1 Drawing Figure

BACKGROUND OF THE VARIETY

1. Field of the Discovery

The present new and distinct variety of almond tree is embraced by Class 30, Plants, of the U.S. Patent Office Manual of Classification.

2. Prior Varieties

Among the existent varieties of almond tree which are known to me, and mentioned herein, is Ne Plus Ultra (unpatented).

ORIGIN OF THE VARIETY

The present variety of almond tree was discovered by me growing, as an open-pollinated chance seedling, on my ranch located near Modesto, Stanislaus County, Calif.; the original tree having particularly come to my attention when such tree was in its third leaf, and at which time I recognized its new and distinctive characteristics, as will hereinafter appear. Upon recognition by me of the novelty of the variety, and its potential for commercial planting, I determined to effect asexual reproduction thereof.

ASEXUAL REPRODUCTION OF THE VARIETY

The present variety of almond tree was asexually reproduced, on my behalf and by a commercial nursery, by scion budding on seedling stock, and such asexual reproductions—in maturity—ran true to the original tree in all respects.

SUMMARY OF THE VARIETY

The herein-claimed variety of almond tree is open, medium size, vigorous, stocky of trunk and branches, both with smooth texture, upright with diverging branches, foliated with medium size, acuminate, acutely pointed, thin, smooth-textured leaves having a crenate, finely serrate margin and small, alternate, green, globose glands, blooms heavily with pink flowers, and is a regular and heavy bearer of large, well-sealed, well-distributed nuts having large kernels.

The herein-claimed variety of almond tree is further characterized, in comparison to the Ne Plus Ultra, by:

The tree has a strong, vigorous, upright growth with a diverging branch pattern, whereas the Ne Plus Ultra tends to be bushy with conflicting branches. The upright growth produces a tree of greater height than the Ne Plus Ultra.

The tree is in bloom, with large, pink flowers, about a week after the Ne Plus Ultra.

The nuts, which mature earlier than any commercial almond variety grown in the same agricultural area, are in harvest two to three weeks earlier than the Ne Plus Ultra.

The nuts are more symmetrical in shape than the Ne Plus Ultra, and the shell texture is similar with smooth cork although slightly lighter in color.

The herein-claimed variety of almond tree is still further characterized by the bearing of nuts which have a large average size and weight which distinguishes them from the nuts of most commercially grown varieties. Also, the kernels are of large average size and weight, being sweet, attractive, and blanching readily.

The herein-claimed variety of almond tree is further characterized by a tree which, in its first summer (while in a nursery row), develops a red to scarlet color of the bark that is exposed to the sun; such color being more intense than generally found on nursery trees of other almond varieties. Additionally, the first and second crops of nuts are mostly on fruit spurs rather than directly on limbs; this being unlike numerous other varieties of almonds.

BRIEF DESCRIPTION OF THE DRAWING

The drawing is an illustration, by photographic reproduction in color, of a twig with leaves and nuts in hull, and—separately—a twig-attached nut in an open hull, nuts out of hull, and kernels out of shell.

DESCRIPTION OF THE VARIETY

The botanical details of this new and distinct variety of almond tree—with color definitions (except those in common color terms) referenced to Maerz and Paul Dictionary of Color (First Edition)—are as follows:

Tree:

*Density.*—Open.

*Size.*—Medium.

*Vigor.*—Vigorous.

Trunk:

*Form.*—Stocky.

*Texture.*—Smooth.

Branches:

*Form.*—Stocky.

*Texture.*—Smooth.

*Lenticels.*—Size: Small. Branching habit: Upright—diverging. Color—New wood: Red—brown. Mature wood: Gray.

Foliage:

*Quantity.*—Medium.

Leaves:

*Size.*—Medium. Average length—4.21".Average width—0.92".

*Shape.*—Acuminate. Acutely pointed.

*Thickness.*—Thin.

*Texture.*—Smooth.

*Margin.*—Crenate. Finely serrate.

*Petiole.*—Medium length. Medium thickness.

*Glands.*—Average number—3.06. Alternate. Small. Globose. Green. Positioned 2.43 on petiole, balance on blade.

*Stipules.*—None.

*Color.*—Top Side—Medium glossy green (22-K-8). Under Side—Lighter dull green (22-L-7).

Bloom:

*Amount of bloom.*—Heavy.

*Color of bloom.*—Pink—pink tone remains for several days.

*Blooming period.*—Medium. About one week after Ne Plus Ultra.

Crop:

*Bearing.*—Regular bearer.

*Productivity.*—Heavy.

*Distribution of nuts on tree.*—Well distributed.

*Harvest period.*—Aug. 29th—31st, 1979. Early—about with first Nonpareil harvest. About two to three weeks earlier than Ne Plus Ultra.

*Tenacity.*—Hangs well on tree. Easy to harvest. Easy to hull.

Hull:

*Outer surface.*—Smooth.

*Form.*—Regular.

*Thickness.*—Thin.

*Flesh.*—Tough.

*Color.*—Biscay green (21-K-5) to olive green (15-L-4).

*Dehiscence.*—Opens freely.

*Splitting.*—Along suture. Freely at base.

Nut:

*Size.*—Large. Average length—39.75 mm. Average width—22.87 mm. Average thickness—17.05 mm. Average weight—8.16 per ounce.

*Form.*—Length/width: Elongated. Width/thickness: Plump.

*Shell.*—Soft. Thick. Smooth. Outer shell: Hard. Inner shell: Hard. Well sealed.

*Color.*—Light brown (13-K-7).

*Pits.*—Large. Numerous. Shallow.

*Base.*—Ventrally oblique.

*Stem scar.*—Large. Obtuse.

*Apex.*—Obtuse. Blunt. Tip recurved.

*Wing.*—Narrow. Thick. Tapered toward base.

*Inner surface.*—Medium colored.

*Ventral streak.*—Light colored. Narrow. Long. Point obtuse.

*Percentage of kernel to nut.*—52.23%.

Kernel:

*Size.*—Large. Average length—30.15 mm. Average width—14.02 mm. Average thickness—7.97 mm. Average weight—16.66 kernels per ounce.

*Form.*—Length/width: Elongated. Width/thickness: Medium.

*Base.*—Ventrally oblique.

*Stem scar.*—Small. Obtuse.

*Apex.*—Obtuse. Blunt. Tip recurved.

*Texture.*—Wrinkled.

*Pellicle.*—Thin.

*Pubescence.*—Medium. Veined.

*Color.*—Buckthorn brown (13-L-8).

*Number of doubles.*—Many—average 15%.

*Defective kernels.*—Some slightly shriveled—10%.

*Flavor.*—Sweet.

*Quality.*—Very good.

Resistance to insects and diseases: No more susceptible than any commercial variety under same growing conditions.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, particularly characterized, in comparison to the Ne Plus Ultra, by a tree of greater height, having open, strong, vigorous, upright growth and a diverging branch pattern; by heavy blooming, with pink flowers, about a week later; and by the regular and heavy bearing of large, well-sealed, more symmetrical nuts in harvest two to three weeks earlier.

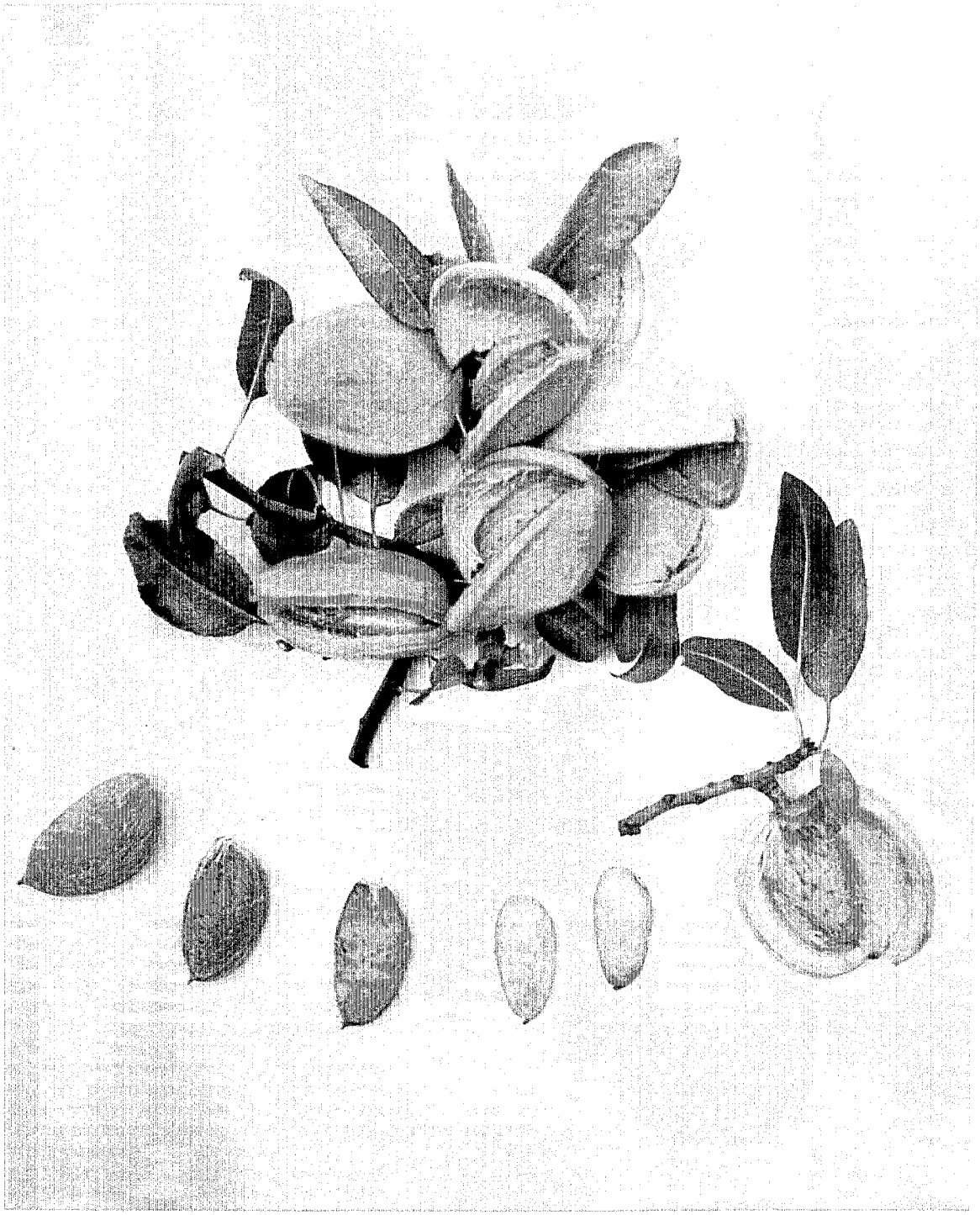

* * * * *